(12) United States Patent
Kim et al.

(10) Patent No.: US 11,932,861 B2
(45) Date of Patent: Mar. 19, 2024

(54) VIRUS-BASED REPLICON FOR PLANT GENOME EDITING WITHOUT INSERTING REPLICON INTO PLANT GENOME AND USES THEREOF

(71) Applicant: INDUSTRY-ACADEMIC COOPERATION FOUNDATION GYEONGSANG NATIONAL UNIVERSITY, Gyeongsangnam-do (KR)

(72) Inventors: Jae Yean Kim, Gyeongsangnam-do (KR); Tien Van Vu, Gyeongsangnam-do (KR); Jihae Kim, Gyeongsangnam-do (KR); Se Jeong Jeong, Gyeongsangnam-do (KR); Hyun Jeong Kim, Gyeongsangnam-do (KR); Seo-Jin Park, Gyeongsangnam-do (KR); Mil Thi Tran, Gyeongsangnam-do (KR); Velu Sivankalyani, Gyeongsangnam-do (KR); Yeon Woo Sung, Gyeongsangnam-do (KR); Thi Hai Duong Doan, Gyeongsangnam-do (KR); Dibyajyoti Pramanik, Gyeongsangnam-do (KR); Mahadev Rahul Shelake, Gyeongsangnam-do (KR); Geon Hui Son, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

( * ) Notice: Subject to any disclaimer, the term of this patent is extended or adjusted under 35 U.S.C. 154(b) by 515 days.

(21) Appl. No.: 17/274,559

(22) PCT Filed: Sep. 10, 2019

(86) PCT No.: PCT/KR2019/011677
§ 371 (c)(1),
(2) Date: Mar. 9, 2021

(87) PCT Pub. No.: WO2020/055084
PCT Pub. Date: Mar. 19, 2020

(65) Prior Publication Data
US 2022/0049263 A1   Feb. 17, 2022

(30) Foreign Application Priority Data
Sep. 11, 2018   (KR) ........................ 10-2018-0108026

(51) Int. Cl.
*C12N 15/82* (2006.01)
(52) U.S. Cl.
CPC ............... *C12N 15/8203* (2013.01); *C12N 2750/12043* (2013.01)
(58) Field of Classification Search
None
See application file for complete search history.

(56) References Cited

U.S. PATENT DOCUMENTS

2014/0273235 A1   9/2014   Voytas et al.

FOREIGN PATENT DOCUMENTS

| KR | 10-2002443 B1 | 7/2019 |
| WO | WO 2016/084084 A1 | 6/2016 |
| WO | WO 2018/047183 A1 | 3/2018 |

OTHER PUBLICATIONS

Wang, Mugui, et al. "Gene targeting by homology-directed repair in rice using a geminivirus-based CRISPR/Cas9 system." Molecular plant 10.7 (2017): 1007-1010. (Year: 2017).*

(Continued)

*Primary Examiner* — Weihua Fan
(74) *Attorney, Agent, or Firm* — The PL Law Group, PLLC

(57) ABSTRACT

A recombinant vector according to an embodiment is for genome editing without inserting a replicon into the plant genome in a $T_0$ generation plant. The recombinant vector includes a geminivirus-based replicon between the sequence of LB (left border) and sequence of RB (right border) of Ti plasmid. A method of genome editing without inserting a replicon into the plant genome in a $T_0$ generation plant according to an embodiment includes transforming a plant cell by inserting a foreign gene to the aforementioned recombinant vector.

4 Claims, 6 Drawing Sheets

Specification includes a Sequence Listing.

(56) References Cited

OTHER PUBLICATIONS

Čermák, Tomáš, et al. "High-frequency, precise modification of the tomato genome." Genome biology 16 (2015): 1-15. (Year: 2015).*

Tóth, Eszter, et al. "Restriction enzyme body doubles and PCR cloning: on the general use of type IIs restriction enzymes for cloning." PloS one 9.3 (2014): e90896. (Year: 2014).*

Office action dated Sep. 2, 2022 from China Patent Office in a counterpart China Patent Application No. 201980059729.7 (all the cited references are listed in this IDS.) (English translation is also submitted herewith.).

Cloning vector pVIR-Nick, complete sequence, GenBank: MG760357.1.

Florian Hahn et al.,"Homology-Directed Repair of a Defective Glabrous Gene in *Arabidopsis* With Cas9-Based GeneTargeting", Frontiers in Plant Science, 2018, pp. 1-13, vol. 9, Article 424, doi: 10.3389/fpls.2018.00424.

Maize streak virus isolate MSV-KNak, complete genome GenBank: EU152256.1.

International Search Report for PCT/KR2019/011677 dated Dec. 20, 2019.

Zaide, S.S. et al., Viral Vectors for Plant Genome Engineering, Frontiers in Plant Science, Apr. 2017, p. 1-6, Article 539, vol. 8.

Baltes, N.J. et al., DNA Replicons for Plant Genome Engineering, The Plant Cell, Jan. 2014, p. 151-163, vol. 26, American Society of Plant Biologists.

Cermak, T. et al., High-frequency, precise modification of the tomato genome, Genome Biology. 2015, vol. 16, document 232, p. 1-14.

* cited by examiner

VIRUS-BASED REPLICON FOR PLANT GENOME EDITING WITHOUT INSERTING REPLICON INTO PLANT GENOME AND USES THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/011677, filed Sep. 10, 2019, which claims priority to the benefit of Korean Patent Application No. 10-2018-0108026 filed in the Korean Intellectual Property Office on Sep. 11, 2018, the entire contents of which are incorporated herein by reference.

BACKGROUND

Technical Field

The present invention relates to a virus-based replicon for plant genome editing without inserting a replicon into the plant genome, and uses thereof.

BACKGROUND ART

Genetic scissors is a cutting-edge breeding technique targeting a plant, and it is a tool for introducing a change in the nucleotide sequence of the internal genome while all foreign genes like genetic scissors used for gene/genome editing are removed from a final product. Genome editing part such as Cas9 (CRISPR associated protein 9) is generally expressed via *Agrobacterium*-mediated transformation and, in this case, T-DNA is inserted into the genome of a plant at $T_0$ or $T_1$ generation to yield gene editing. After that, according to genetic separation at $T_1$ or $T_2$ generation, a genome-edited plant having no insertion of T-DNA is selected.

The present invention relates to a technique for editing plant genome in which the genome editing is carried out by using a virus-based replicon while no replicon is inserted into a plant genome, and the replicon is removed from the cell such that the replicon is already not included in the events selected at $T_0$ generation. As a replicon for this technique, Bean Yellow Dwarf Virus-based replicon (for dicot plants) and Maize Streak Virus-based replicon (for monocot plants) are used. The use of the replicon of the present invention has the advantage that effective gene editing can be achieved in crops that reproduce by vegetative reproduction instead of sexual reproduction (i.e., seed propagation). The method of removing genetic scissors via Mendel's law of segregation at $T_1$ generation is generally applicable for the crops that reproduce by sexual reproduction while, for the crops that reproduce by vegetative reproduction, it remained impossible to remove the genetic scissors. However, with the use of the replicon of the present invention, it would be possible to have effective gene editing in the crops that reproduce by vegetative reproduction. Furthermore, although the gene editing is immediately obtained at $T_0$ generation when the replicon vector system of the present invention is used, by ensuring the events in which foreign genes are not inserted, new breeding may be achieved faster than obtaining such events at $T_1$ or $T_2$ generation according to conventional techniques. In addition, as the gene editing is caused by genetic scissors which are transiently expressed in a state in which the foreign gene is not inserted at all into the plant genome, it is considered that, unlike the conventional techniques of genetic scissors, a non-GMO type technique is employed even in a process state. Thus, it is believed to be advantageous in terms of overcoming regulatory challenges and restrictions.

Meanwhile, Korean Patent Application Publication No. 2017-0081268 discloses "Nucleic acid constructs for genome editing" relating to plants cells comprising a tobacco rattle virus (TRV) sequence and a nucleic acid sequence encoding a single guide RNA (sgRNA) that mediates sequence-specific cleavage in a target sequence of a genome of interest, and use of the plant cells for gene editing. However, the virus-based replicon for plant genome editing without inserting a replicon into the plant genome of the present invention, and uses thereof are not described.

SUMMARY

The present invention is devised under the circumstances that are described above. As a result of carrying out genome editing of a plant by using geminivirus-based replicon, the inventors of the present invention found that genome editing is achieved in a $T_0$ event plant while the replicon is not inserted at all in the plant genome, and thus the inventors completed the present invention.

To achieve the purpose described above, the present invention provides a recombinant vector for genome editing without inserting a replicon into a plant genome in a $T_0$ generation plant, said recombinant vector including a geminivirus-based replicon between the sequence of LB (left border) and sequence of RB (right border) of Ti plasmid.

The present invention further provides a method of genome editing without inserting a replicon into the plant genome in a $T_0$ generation plant in which the method includes transforming a plant cell by inserting a foreign gene to the aforementioned recombinant vector.

The present invention still further provides a composition for genome without inserting a replicon into plant genome editing in a $T_0$ generation plant in which the composition comprises the aforementioned recombinant vector as an effective component.

The present invention relates to a system of using virus-based replicon in plant plasmid form for editing plant genome, in which the replicon used in the present invention is not inserted to the genome of a plant but lost in $T_0$ generation. Thus, the system is a non-GMO type technique that allows a shorter breeding process and does not involve any insertion of a foreign gene into the genome of a plant.

DETAILED DESCRIPTION

Figure 1:
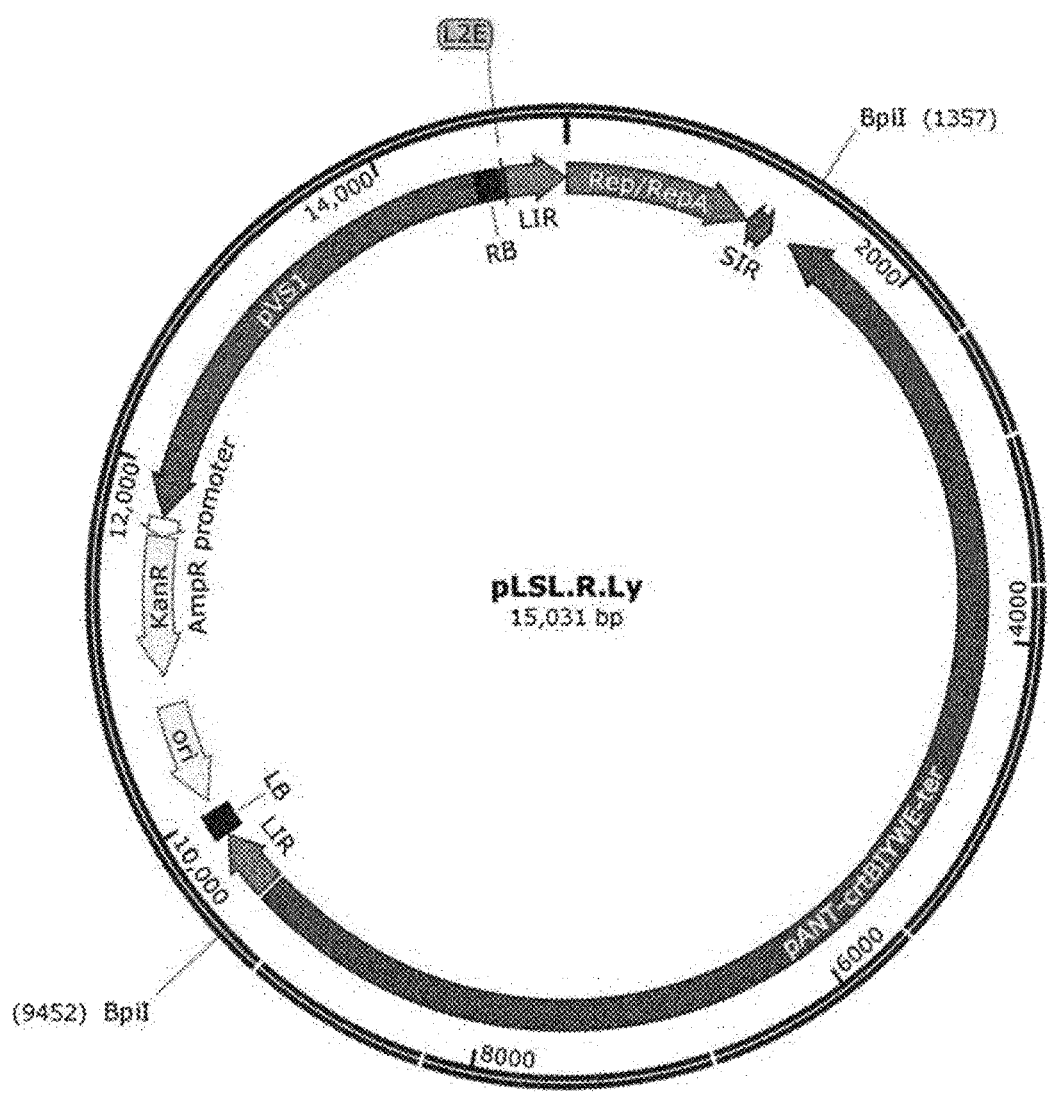
FIG. 1 shows a vector map of the Bean Yellow Dwarf Virus (BeYDV)-based pLSL.R.Ly vector (Golden Gate Level 2 vector).

To achieve the purpose described above, the present invention provides a recombinant vector for genome editing without inserting a replicon into the plant genome in a $T_0$ generation plant, said recombinant vector including a geminivirus-based replicon between the sequence of LB (left border) and sequence of RB (right border) of Ti plasmid.

As described herein, the term "recombinant" indicates that, in a cell, an exogenous nucleotide is replicated or expressed, or a peptide, an exogenous peptide, or a protein encoded by an exogenous nucleotide is expressed. A recombinant cell can express a gene or a gene fragment, which is not found in the natural-state cell, in the form of a sense or antisense. In addition, the recombinant cell can express a gene that is found in the natural state, but the gene has been modified and re-introduced into the cell by an artificial means.

As described herein, the "vector" is used for indicating a means for delivering DNA fragment(s) or genetic molecules to cells. Vector allows independent replication of DNA and it can be re-produced in host cells. The term "delivery vehicle" is used interchangeably with "vector". The term "expression vector" means a recombinant vector that contains a target coding sequence and a suitable gene sequence essentially required for expressing an operably-linked coding sequence in a specific host organism. The recombinant vector indicates a bacteria plasmid, a phage, a yeast plasmid, a plant cell virus, a mammalian cell virus, or other vector. In general, as long as it can be replicated and stabilized in a host, any plasmid or vector can be used.

With regard to the recombinant vector according to one embodiment of the present invention, the geminivirus can be BeYDV (Bean Yellow Dwarf Virus) or MSV (Maize Streak Virus), but it is not limited thereto. BeYDV is used for producing a replicon for a dicot plant and MSV is used for producing a replicon for a monocot plant.

With regard to the recombinant vector of the present invention, the replicon may have LIR (long intergenic region); promoter; Rep/RepA protein-coding sequence; terminator; SIR (short intergenic region); MCS (multiple cloning site) to which a foreign gene to be expressed can be inserted; SIR; and LIR that are sequentially connected, but it is not limited thereto.

In virus, LIR can play a role of replication origin and promoter and SIR can play a role of terminator.

In general, the smaller the replicon size is, the higher the copy number is obtained, and since a higher probability of homologous recombination is obtained as the copy number of a template increases, the constitution of the replicon can be controlled by considering various factors.

With regard to the recombinant vector according to one embodiment of the present invention, the replicon can be a replicon consisting of the nucleotide sequence of BeYDV-based SEQ ID NO: 1 or a replicon consisting of the nucleotide sequence of MSV-based SEQ ID NO: 2, but it is not limited thereto.

As described herein, the term "replicon" means a replication unit capable of having voluntary control, and the replication unit is a continuous DNA molecule in which the replication is initiated at specific site within a molecule and terminated after sequential progress. All of the plasmid, viral DNA, and bacterial chromosome are a single replication unit.

It was shown by Baltes et. al. (2014, Plant Cell 26 (1):151-163) that, according to amplification of a HR (homologous recombination) template by using ZFN (Zinc Finger Nuclease) and geminivirus-based virus replicon, the HR efficiency can be remarkably improved in a tobacco plant. The geminivirus replicon containing ZFN and HR template was added in T-DNA and, after the introduction to a tobacco plant mediated by *Agrobacterium* and rolling-circle replication, a replicon in circular form is produced and, according to induction of DSB in defective GUS target gene by expressing ZFN, HR is induced to occur by the HR template added in the replicon.

With regard to the replicon of the present invention, the aforementioned MCS may be composed of a restriction enzyme such as BsmBI, AarI or BpiI, but it is not limited thereto. The restriction enzyme such as BsmBI, AarI or BpiI is a Type IIs restriction enzyme for Golden gate cloning.

The genome editing based on the use of a virus-based replicon may allow genome editing based on the mechanism of homologous recombination.

In the aforementioned MCS according to the present invention, a template DNA sequence for genome editing can be cloned. Alternatively, a template DNA sequence for genome editing; a sequence encoding one or more nucleic acid hydrolases selected from a group consisting of Cas9 (CRISPR associated protein 9), Cpf1 (CRISPR from Prevotella and Francisella 1), TALEN (Transcription activator-like effector nuclease), ZFN (Zinc Finger Nuclease), and their functional homologs; and a guide RNA for inducing the nucleic acid hydrolase to a target genome site desired for editing, or the like can be cloned in the MCS, but it is not limited thereto.

As a result of comparing the efficiency of homologous recombination depending on a difference between Cas9 and Cpf1, the inventors of the present invention found that Cpf1 has higher efficiency of homologous recombination events than Cas9.

The present invention further provides a method of genome editing without inserting a replicon into the plant genome in a $T_0$ generation plant in which the method includes transforming a plant cell by inserting a foreign gene to the recombinant vector of the present invention.

The recombinant vector of the present invention is the same as described above. As the replicon is removed from $T_0$ event cells in which genome editing has occurred, it is found that effective genome editing can be achieved even in crops propagated by vegetative reproduction instead of sexual reproduction.

The replicon according to one embodiment of the present invention can be a replicon consisting of the nucleotide sequence of SEQ ID NO: 1 or SEQ ID NO: 2, but it is not limited thereto.

The present invention still further provides a composition for genome editing without inserting a replicon into the plant genome in a $T_0$ generation plant in which the composition comprises the recombinant vector of the present invention as an effective component. As the composition of the present invention comprises, as an effective component, a recombinant vector including virus-based replicon, which allows an editing event of a target gene without having the replicon itself inserted to the plant genome, only the editing of the desired gene can be achieved without having insertion of the replicon to genome in $T_0$ generation plant.

Hereinbelow, the present invention is explained in detail in view of the Examples. However, it is evident that the following Examples are given only for exemplification of the present invention and by no means the present invention is limited to the following Examples.

Materials and Methods

1. Experimental Materials

Materials used in the present invention are described in the following Table 1.

TABLE 1

Experimental materials, reagents, and tools used in the present invention

| Name | Source |
| --- | --- |
| Plant | |
| Tomato variety Cultivar Hongkwang | Local company |
| Bacteria | |
| *Escherichia coli* 10-beta | NEB, USA |
| *Agrobacterium tumefaciens* GV3101::pMP90 | Kyungsang Univ., South Korea |
| DNA vector | |
| pTC147 | Addgene, USA |
| pTC217 | Addgene, USA |
| pControl 2.6 (8161.1) | Vector kept in the lab |
| Golden Gate tool kit | Addgene, USA |
| MoClo Tool kit | Addgene, USA |
| Reagents | |
| dNTPs | ThermoFisher Scientific, USA |
| Phusion Taq DNA polymerase | ThermoFisher Scientific, USA |
| Pfu DNA polymerase | ThermoFisher Scientific, USA |
| T4 DNA ligase | NEB, USA |
| Restriction enzymes (BpiI, BsaI and others) | NEB, USA |
| T7E1 endonuclease | NEB, USA |
| Plant hormones; Acetosyringone; Hydrocarbon; | Sigma, USA; |
| β-D Glucuronide (X-Gluc); Chemicals for plant tissue culture; MS salts and vitamins; MS salts and B5 vitamins, PhytoAgar, Maltose. | DUCHEFA Biochemie B.V., Netherland |
| Water | Treated with Millipore system |
| Kit | |
| CloneJET ™ PCR cloning | ThermoFisher Scientific, USA |
| Plasmid DNA isolation kit (mini and midi) | BIOFACT, South Korea; Qiagen, Germany |
| Total genomic DNA isolation kit (mini preps) | Qiagen, Germany |

2. Cloning 2.1 DNA Fragment Amplification by Using PCR

By using Phusion Taq polymerase (high fidelity) according to the manufacturer's protocol, PCR reaction was carried out after mixing a specific primer (final conc. 0.4 µM), dNTPs (final conc. 0.2 mM), and a template (10 to 20 ng of genomic DNA or 0.1 to 0.5 ng of purified DNA/reaction). As for the water used for PCR reaction, water having electric conductivity of less than 2 µS/cm and being free of DNase, RNase, or protease was used. The PCR product was identified by loading onto 0.8% agarose gel. After excising the gel at the part of a band with the expected size, it was purified by using QIAquick Gel Extraction Kit (Qiagen). The concentration of the PCR product was measured by using Nanodrop 2.0 (ThermoFisher Scientific).

2.2 Golden Gate Digestion-Ligation Setup

Conditions of the enzyme treatment (digestion) and ligation for Golden gate assembly were set as those described in the following Table 2.

TABLE 2

| Conditions of Digestion-Ligation | | |
| --- | --- | --- |
| Components | Required amount (fmol) | 1× |
| 10 × T4 DNA buffer | | 1.5 |
| Insert | 20 | x |

TABLE 2-continued

| Conditions of Digestion-Ligation | | |
| --- | --- | --- |
| Components | Required amount (fmol) | 1× |
| Vector | 13 | y |
| T4 DNA ligase | | 0.5 |
| BsaI or BpiI or BsmBI | | 0.5 |
| H$_2$O | | up to 15 |
| Total | | 15 (µl) |

For a case in which BsaI or BpiI is used, the reaction program for gene amplification is the same as those described in the following Table 3. For a case in which BsmBI is used, the reaction program for gene amplification is the same as those described in the following Table 4.

TABLE 3

Conditions of amplification reaction (BsaI or BpiI)

| Stage | Temperature (° C.) | Time (minutes) | Repetition number | Remarks |
|---|---|---|---|---|
| 1 | 37 | 15 | 1 | Pre-digestion |
| 2 | 37<br>16 | 2<br>5 | 25-40 | Digestion-ligation |
| 3 | 37 | 5 | 1 | Post-digestion |
| 4 | 50 | 5 | 1 | Post-digestion |
| 5 | 80 | 5 | 1 | Denaturation |

TABLE 4

Conditions of amplification reaction (BsmBI)

| Stage | Temperature (° C.) | Time (minutes) | Repetition number | Remarks |
|---|---|---|---|---|
| 1 | 42 | 15 | 1 | Pre-digestion |
| 2 | 42<br>16 | 2<br>5 | 25-40 | Digestion-ligation |
| 3 | 42 | 5 | 1 | Post-digestion |
| 4 | 50 | 5 | 1 | Post-digestion |
| 5 | 80 | 5 | 1 | Denaturation |

2.3 Escherichia coli Transformation

*Escherichia coli* 10β strain was transformed with the digestion-ligation mixture. After that, the transformed *Escherichia coli* and 15 μl of XGAL (5-bromo-4-chloro-3-indolyl-β-D-galactopyranoside, 20 mg/ml) were spread on an LB solid medium containing 125 mg/ml carbenicillin or ampicillin. After culture overnight, white positive colonies were identified.

To determine the construct ratio within the colony, for each construct, white colonies were inoculated to an LB liquid medium containing 50 mg/L streptomycin (for identifying level 0 cloning), an LB liquid medium containing 125 mg/L carbenicillin (for identifying level 1 cloning), or an LB liquid medium containing 50 mg/L kanamycin (for identifying level 2 or 3 cloning) followed by culture. Then, plasmids were isolated and treated with a suitable restriction enzyme. Colonies containing the plasmid, which exhibits the expected cut size, were classified into separate positive clones.

2.4 Sequencing

Solgent (South Korea) was requested to carry out sequencing of the clones, two positive clones for each construct. Results of the sequencing were analyzed first, and then the cloning was carried out.

3. Construction of BeYDV (Bean Yellow Mosaic Virus)-Based Replicon Receptor Vector To construct level 2 vector containing BeYDV replicon with Rep/RepA, which has been adjusted for expression, within LIR-SIR-LIR (i.e., for using the vector as Golden gate level 2 receptor), BpiI cloning site (TGCC . . . GGGA) was inserted between LIR-SIR and LIR. LIR-SIR and LIR were used after they have been cloned from pLSLR vector.

For the cloning reaction of pLSL, which is a vector containing LIR-SIR-LIR with BpiI cloning site between SIR-LIR, the following DNA fragment was sequentially assembled by using BpiI to generate a sticky end followed by ligation using T4 DNA ligase:

a) PCR product: BpiI (TGCC)-LIR-SIR-(TGCC) BsaI. (GCAA)BpiI
b) PCR product: BpiI (GCAA).BsaI (GGGA)-LIR-BpiI (ACTA)
c) pICH41744 end linker vector: BpiI (ACTA)-L3E-(GGGA)BpiI
d) Level 2 acceptor: pAGM4673 or pAGM4723 (TGCC . . . GGGA).

After that, for cloning pLSL.MCS1 containing MCS (multicloning site) between LIR-SIR, the following DNA fragment was ligated by integration at MCS1 site of pLSL vector:

a) pLSL cleaved by AscI and BstXI.
b) MCS1 (MCSf1 and MCSr1 were mixed and annealed).

After that, to construct a vector (pLSL.Ly) having lycopene-expressing cassette as a cloning marker introduced to pLSL.MCS1, the following DNA fragment was ligated:

a) pLSL.MCS1 cleaved by BpiI.
b) pAGM4723 cleaved by BpiI and separated lycopene fragment.

After that, for cloning pLSL.R.Ly vector in which Rep/RepA coding sequence has been cloned under the control of LIR, the following DNA fragment was ligated inside the replicon:

a) pLSL.Ly cleaved by BsaI.
b) Rep/RepA PCR product produced by RRA-F4/RRA-R4 primer.

Figure 2:
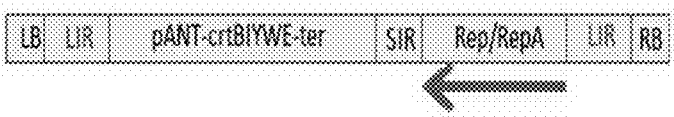
FIG. 2 shows the T-DNA schematic diagram of pLSL.R.Ly vector and nucleotide sequence of LIR-REp/REpA-SIR.
Figure 3:
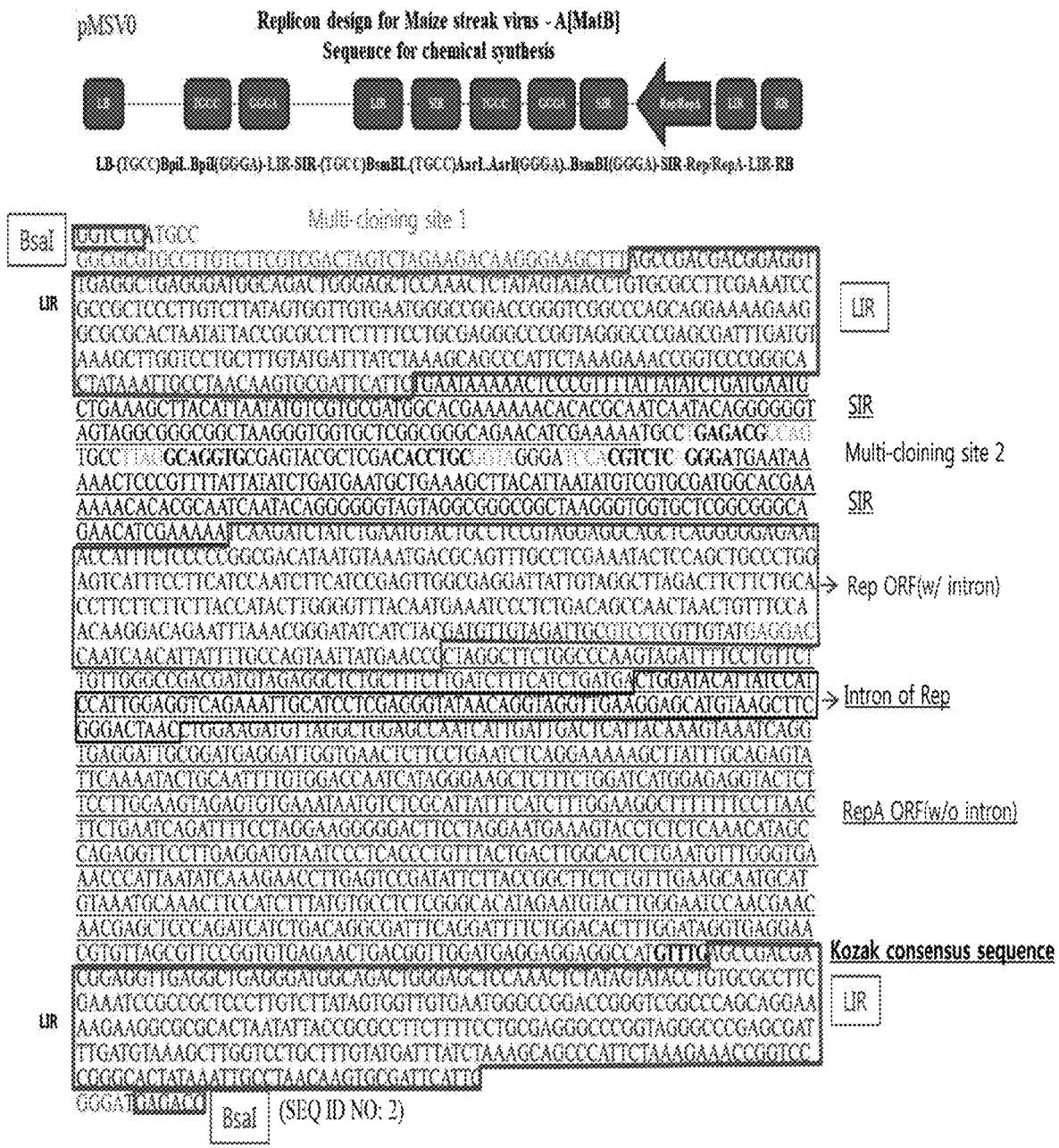
FIG. 3 shows the schematic diagram of Maize Streak Virus (MSV)-based replicon (pMSV0). When the intron does not operate, the Rep/RepA coding DNA part is coded into ORF with short RepA. When the intron is cleaved so that the rear part operates as an exon, Rep protein is produced with long ORF. The protein coding ORF is described in reverse sequence.

A construct containing crRNA, 35S-Cpf1, donor template, or the like in which genes relating to the production of lycopene (i.e., Ly) are removed from the pLSL.R.Ly vector (FIG. 1 and FIG. 2) as constructed in the above was cloned by Golden gate assembly method (clone named 8161.1), and used for the following experiments.

4. Tomato Transformation

Cotyledon explant originating from tomato (Hongkwang variety) cultivated under in vitro conditions was transformed by using *Agrobacterium* containing the construct of the present invention. Briefly, sterilized seeds of Hongkwang variety were cultured for 7 days under light/dark cycle of 16 hour-light/8 hour-dark, 25±2° C. conditions in 1/2×MSO medium (2.2 g MS salts+B5, 20 g sucrose, 0.5 g MES (pH=5.7), 7.5 g agar for 1 L). Thereafter, seedlings were collected and cotyledon leaves were cut to a size of 0.2 to 0.3 cm. Each fragment (i.e., explant) was then subjected to a pre-treatment by applying it for 1 hour to a flat plate medium containing PREMC media (2.2 g MS salts+B5, 30 g maltose, 0.1 g Ascorbic acid, 1.952 g MES, 0.2 mg IAA (pH=5.5), 7.5 g agar for 1 L; after sterilizing the mixture, it was added with 1.0 mg Zeatin trans-isomer, 1 ml Putrescine (1 mM), and 100 μM acetosyringone (AS)). Tiny holes were created on the pre-treated explant by poking, and, according to a reaction for 20 minutes at room temperature with *Agrobacterium tumefaciens* GV3101::pMP90 strain comprising the construct of the present invention, the transformation was carried out. *Agrobacterium* GV3101::pMP90 strain used for the transformation was subjected to overnight primary culture under stirring at 30° C. in an LB medium containing appropriate antibiotics. Then, from the culture broth which has an $OD_{600}$ value of 0.6 to 0.8 or so, cells were collected by centrifuge. Cell pellets were suspended in an ABM-MS liquid medium containing 200 μM AS, and then used for the transformation of tomato explant.

The tomato explant transformed with the *Agrobacterium* was transferred to a co-culture medium (ABM-MS medium, 8 g/L agar, 200 μM AS) and cultured for 2 days at 25° C. After transfer to a non-selective medium (NSEL) followed by culture for 5 days, the explant was transferred again to a selective medium (SEL5) followed by culture. The subculture of the explant transformed in selective medium was carried out with an interval of 10 days to have the optimum regeneration efficiency. Once the new shoot has sufficient length (1.5 to 3.0 cm), it was transferred to a medium for rooting to induce growth to a complete plant. The complete plant grown in the medium for rooting was then transferred to a vermiculite pot and solidified before it is transferred again to the soil in greenhouse which is under the light/dark cycle of 16 hour-light/8 hour-dark, 26±2° C. temperature.

TABLE 5

Composition of medium used for culturing tomato explant

| AMB (for 1 L) | MS (for 1 L) | ABM-MS | NSEL (for 1 L) | SEL5 (for 1 L) |
|---|---|---|---|---|
| $K_2HPO_4$: 2.212 g<br>$KH_2PO_4$: 1.130 g<br>$NH_4NO_3$: 1.496 g<br>KCl: 0.149 g<br>$MgSO_4$: 0.308 g<br>$CaCl_2$: 0.015 g<br>$FeSO_4$: 0.003 g<br>Glucose: 20 g<br>MES: 3.904 g<br>pH = 5.5 | MS salts + B5 vitamins: 2.2 g<br>Sucrose: 5 g<br>pH = 5.5 | Mix ABM and MS as 1:1 ratio. For semisolid ABM-MS, add 8 g/L of agar. Autoclave then add:<br>Zeatin trans-isomer: 1.0 mg/L<br>IAA: 0.2 mg/L<br>putrescine (1 mM): 1 ml<br>AS (200 μM) | MS salts + B5 vitamins: 4.4 g<br>MES: 0.976 g<br>Maltose: 30 g<br>IAA: 0.2 mg<br>pH = 5.7<br>Agar: 8 g<br>Autoclave then add:<br>Zeatin trans-isomer: 2.0 mg<br>Timentin: 300 mg<br>Putrescine (1 mM): 1 ml | MS salts + B5 vitamins: 4.4 g<br>MES: 0.976 g<br>Maltose: 30 g<br>IAA: 0.5 mg<br>pH = 5.7<br>Agar: 8 g<br>Autoclave then add:<br>Zeatin trans-isomer: 2.0 mg<br>Kanamycin: 80 mg<br>Timentin: 300 mg<br>Putrescine (1 mM): 1 ml |

5. Analysis of $T_0$ Tomato Transformant

Leaves of the tomato transformant were collected and, by using DNeasy Plant mini kit (Qiagen) according to the manufacturer's protocol, total genomic DNA was extracted. The occurrence of the homologous recombination event in $T_0$ plant was determined by PCR analysis using the extracted gDNA as a template and the primers that are specific to the left or right junction of the replicon. By determining the existence of a circular DNA, the presence or absence of the replicon inside $T_0$ event plant was examined. The Actin gene was employed as an internal reference gene. To determine the sequence which has been exchanged via the homologous recombination with replicon junction, the sequence of the PCR product was analyzed by Sanger method.

[TABLE 6]

Information of primers used for PCR analysis for determining an occurrence of homologous recombination by replicon and the presence or absence of replicon

| Target | Primer | Sequence (5'→3') | product size |
|---|---|---|---|
| Left junction | UPANT1-F1 | TGCGATGATCTACGGTAACA AA (SEQ ID NO: 4) | 1485 bp |
| | NPTII-R1 | GCGTGCAATCCATCTTGTTC (SEQ ID NO: 5) | |
| Right junction | ZY010F | ACGTAAGGGATGACGCACA (SEQ ID NO: 6) | 1380 bp |
| | TC140R | TACCACCGGTCCATTCCCTA (SEQ ID NO: 7) | |
| ANT1 control | TC140F | GGAAAATGGCATCTTGTTCC C (SEQ ID NO: 8) | 1056 bp |
| | TC140R | TACCACCGGTCCATTCCCTA (SEQ ID NO: 7) | |
| Replicon | GR-F1 | TTGAGATGAGCACTTGGGAT AG (SEQ ID NO: 9) | 557 bp |
| | pCf.ANT1-R4 | ACCTCAACGACGCAAGTATT (SEQ ID NO: 10) | |

Figure 4:
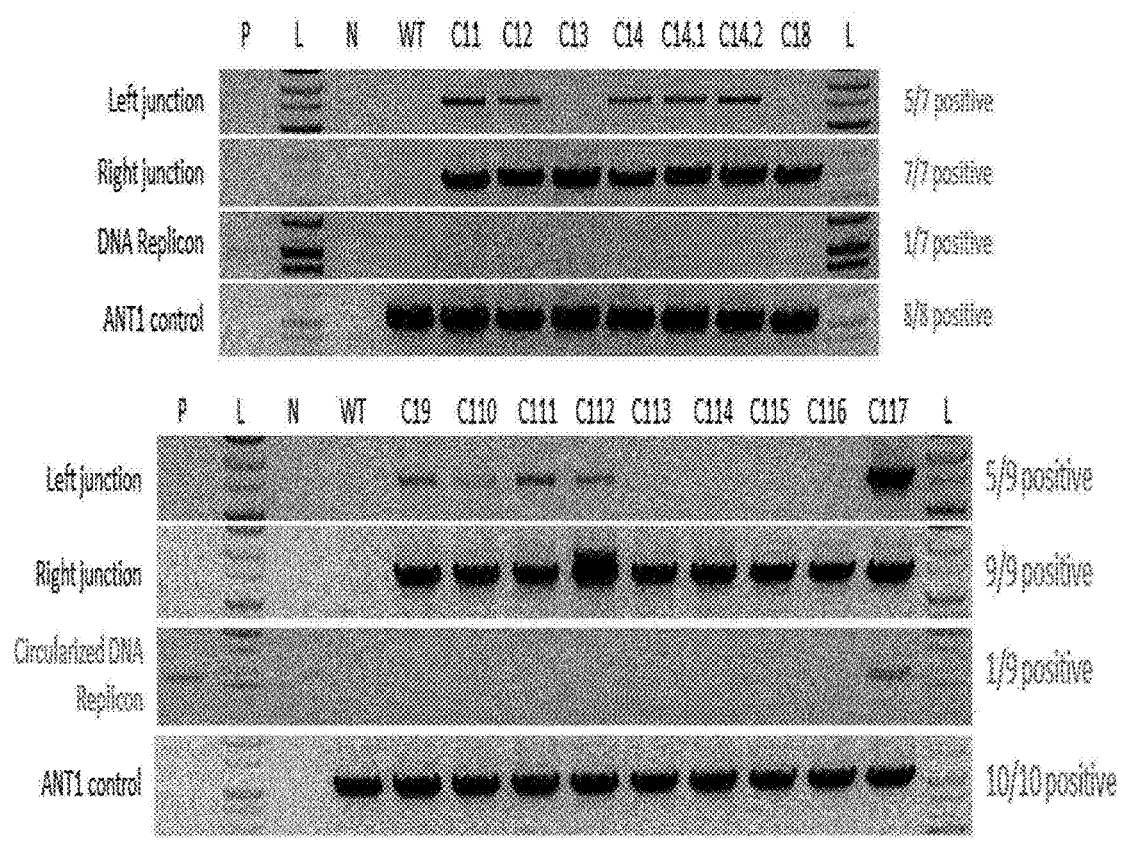
FIG. 4 shows the result of determining the success or failure of genome editing of a tomato $T_0$ plant for which genome editing has been carried out by using pLSL.R.Ly vector (i.e., for determining an occurrence of homologous recombination) and the presence or absence of the replicon.
Figure 5:
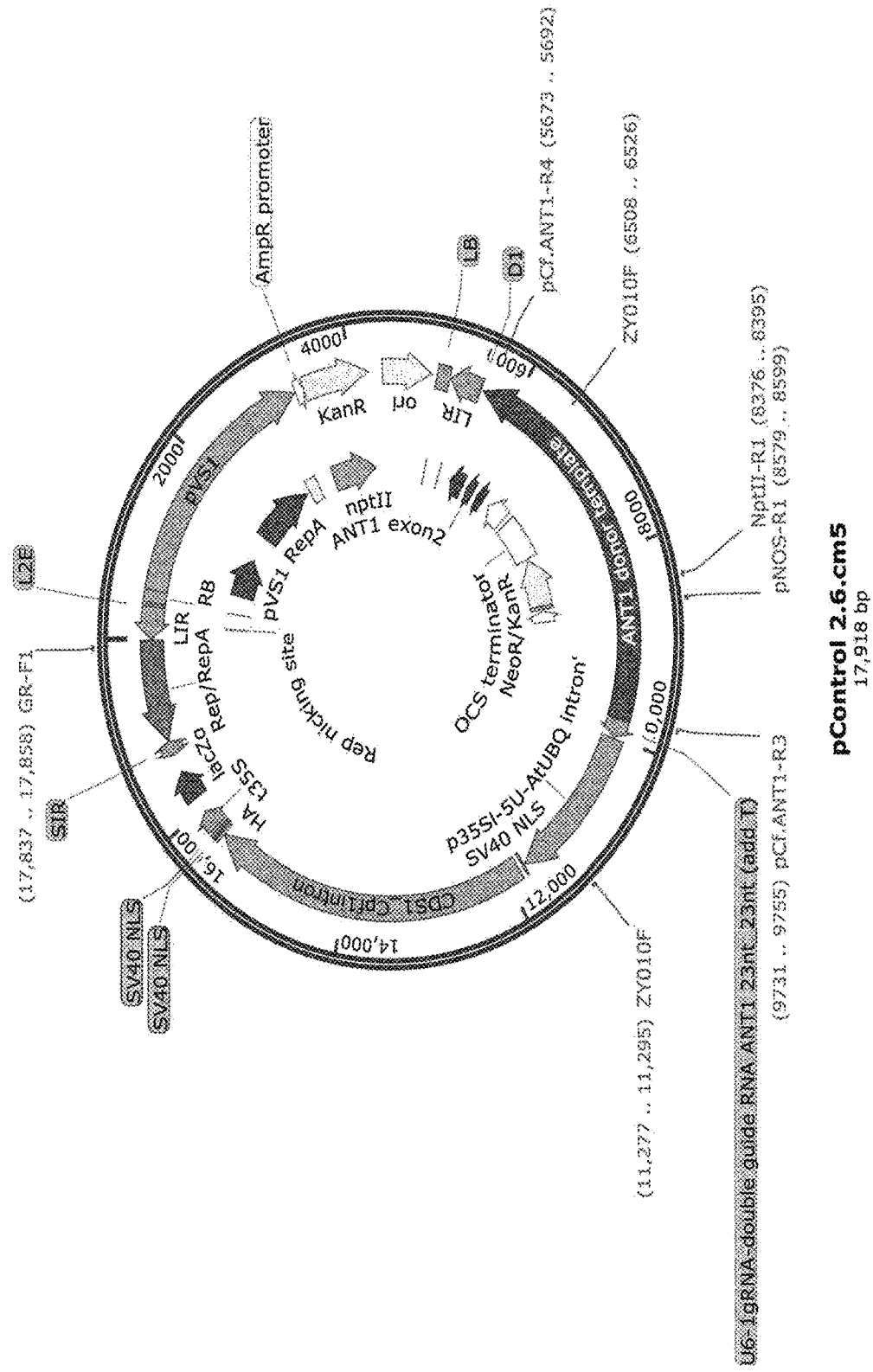
FIG. 5 shows the vector map of pControl 2.6 (8161.1).
Figure 6:
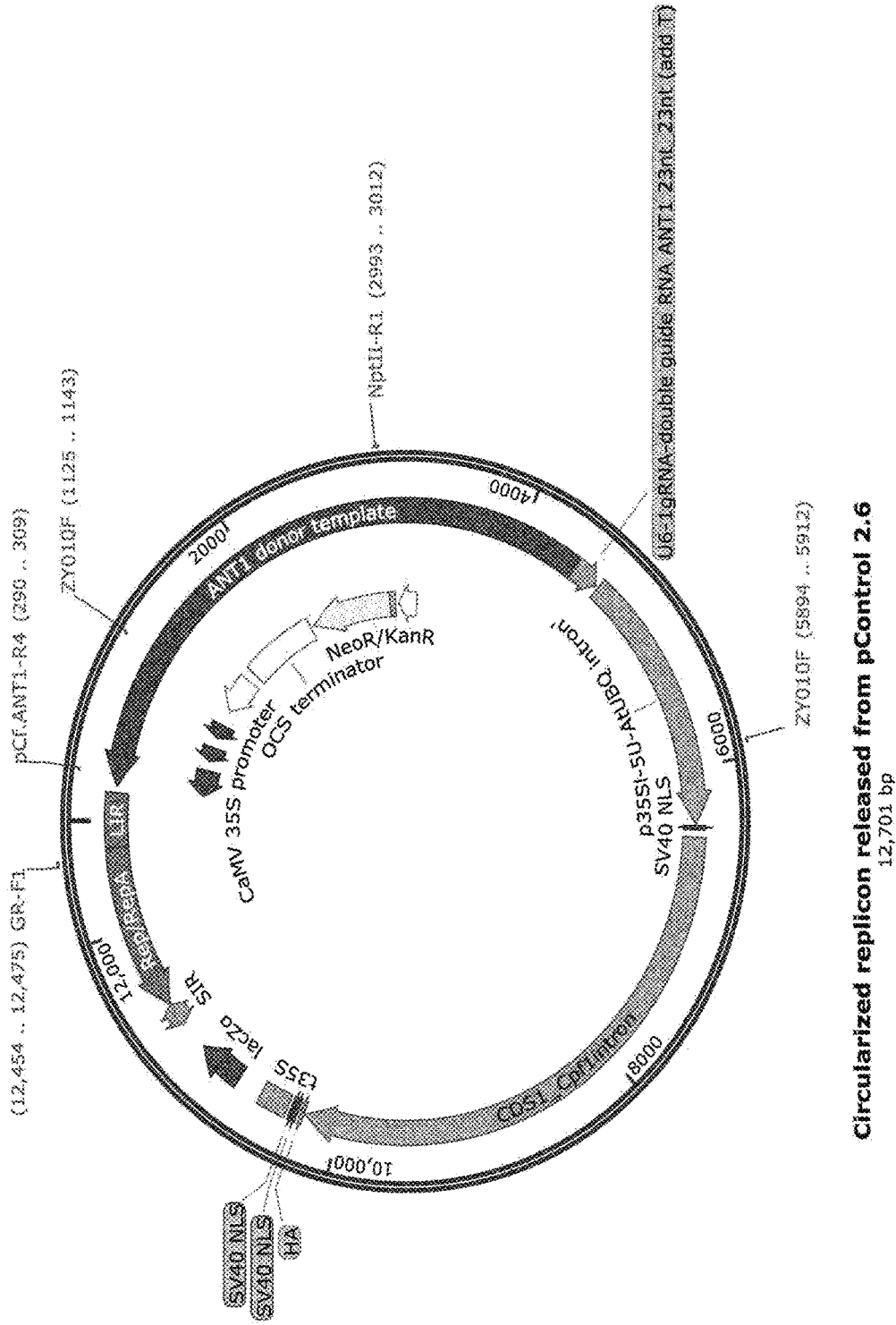
FIG. 6 shows a map of the replicon released from pControl 2.6 (8161.1) vector.

Example 1. Determination of the Presence or Absence of Replicon in $T_0$ Tomato Transformant As a result of performing transformation of a tomato plant by using the virus-based replicon of the present invention, it was found that, from the all sixteen $T_0$ tomato plants tested, a PCR amplification product for the right junction was identified, indicating that homologous recombination has occurred in the all sixteen plants. From ten plants, a PCR amplification product for the left junction was also identified, indicating that complete homologous recombination has occurred in those ten plants. Interestingly, a circular DNA was identified only from two plants (i.e., C11 and C117) among the sixteen plants, and thus it was recognized that, in the remaining fourteen plants, the replicon used for transformation is not inserted into the genome of $T_0$ event plant (FIG. 4). Namely, it is contemplated that, by using the replicon of the present invention, genome editing can be effectively carried out even in crops that reproduce by vegetative reproduction instead of sexual reproduction (i.e., seed propagation).

A sequence listing electronically submitted with the present application on Mar. 9, 2021 as an ASCII text file named 20210309_Q49321GR02_TU_SEQ, created on Mar. 9, 2021 and having a size of 9,000 bytes, is incorporated herein by reference in its entirety.

What is claimed is:

1. A recombinant vector for genome editing without inserting a replicon into plant genome in a $T_0$ generation plant, the recombinant vector including a geminivirus-based replicon between the sequence of LB (left border) and sequence of RB (right border) of Ti plasmid,
   wherein the geminivirus is BeYDV (Bean Yellow Dwarf Virus),
   wherein the replicon has a first long intergenic region (LIR), a Rep/RepA protein-coding sequence, a short intergenic region (SIR), a CaMV 35S terminator, a Cpf1 coding sequence, a CaMV 35s promoter having AtUBQ intron, U6-double gRNAs, a first template DNA site for gene-editing, a NOS promoter, NPTII coding sequence, a OCS (octopine synthase) terminator, a CaMV 35S promoter, a second template DNA site for gene-editing, and a second long intergenic region (LIR) that are sequentially connected.

2. A recombinant vector for genome editing without inserting a replicon into plant genome in a $T_0$ generation plant, the recombinant vector including a geminivirus-based replicon between the sequence of LB (left border) and sequence of RB (right border) of Ti plasmid,
   wherein the replicon has LIR (long intergenic region); promoter; Rep/RepA protein-coding sequence; terminator; SIR (short intergenic region); MCS (multiple cloning site) to which a foreign gene to be expressed can be inserted; SIR; and LIR that are sequentially connected,
   wherein the replicon consists of the nucleotide sequence of SEQ ID NO: 1 or SEQ ID NO: 2.

3. A method of genome editing without inserting a replicon into the plant genome in a $T_0$ generation plant, the method comprising transforming a plant cell by inserting a foreign gene to the recombinant vector of claim 1.

4. A composition for genome editing without inserting a replicon into the plant genome in a $T_0$ generation plant, the composition comprising the recombinant vector of claim 1 as an effective component.

* * * * *

SEQUENCE LISTING

<160> NUMBER OF SEQ ID NOS: 10

<210> SEQ ID NO 1
<211> LENGTH: 1610
<212> TYPE: DNA
<213> ORGANISM: Artificial Sequence
<220> FEATURE:
<223> OTHER INFORMATION: pLSL.R.Ly T-DNA

<400> SEQUENCE: 1

```
gagggtcgta cgaataattc gtatccaacg gaaatacctg atacaatata cgctccatca      60
aataccatca catcgtatat gcttttatag tgtgaacacc tttaaccct gtgggcggga     120
aattttctac tttaaatctg gaccgctcgt gctaaagcac tcgcgataag ggggggccac    180
gccggtaata ttaaattcgg cgtgggcccc cccttgtcgc aaagacttcg tctttaagta    240
aattccacgt cattttccac tatctattaa aatgaccaaa ataccctgc ctccatgcct     300
ccacgccggt tataagatag agtttgaggc aaccctcgg agtcacaaca actcccaaaa     360
tgccttctgc tagtaagaac ttcagactcc aatctaaata tgttttcctt acctatccca    420
agtgctcatc tcaaagagat gatttattcc agtttctctg ggagaaactc acaccttttc    480
ttattttctt ccttggtgtt gcttctgagc ttcatcaaga tggcactacc cactatcatg    540
ctcttctcca gcttgataaa aaaccttgta ttagggatcc ttcttttttc gattttgaag    600
gaaatcaccc taatatccag ccagctagaa actctaaaca agtccttgat tacatatcaa    660
aggacggaga tattaaaacc agaggagatt tccgagatca taaggtttct cctcgcaaat    720
ctgacgcacg atggagaact attatccaga ctgcaacgtc taaggaggaa tatcttgaca    780
tgatcaagga agaattccct catgaatggg caacaaagct tcaatggctg gaatattcag    840
ccaacaaatt attccctcca caacctgaac cgtatgtgtc gcccttcaca gaatcagatc    900
ttcgctgcca cgaagatcta cactcctgga gggaaaccca tctataccat gtaagcatag    960
acgcttatac ttacatacat cctgtctcat accaacaagc tcaatctgac cttgaatgga   1020
tggccgattt aacaaggaca atggaaggaa tggaatccga caccccagcc tctacatctg   1080
cggaccaact cgtaccggaa agaccacctg ggctagaagt ctcggacgac acaactattg   1140
gaacggtacc atcgatttca ccaactacga tgaacacgcc acctataata tcatcgacga   1200
catcccttc aagttcgtcc cattgtggaa gcaattaata ggttgccagt ctgatttcac   1260
tgtcaacct aaatatggaa aaagaagaa aataaaaggt gggatccctt ctataattct    1320
ttgcaatcct gacgaggact ggatgttatc aatgacaagt caacagaagg attactttaa   1380
agataattgc gtcacccact acatgtgtga cggggagact ttttttgctc gggaatcgtc   1440
gagtcactga ggcaacgtgc ctctcctcat acgagtttat ctaaagtgat tatttttttt   1500
ggggtgtttg tttttggatt gtcttttttt gtttatttcg tgtgttatgt aacatatgta   1560
atttctatct acttgcacaa tgaaatatat tcataaaata atcattttat                1610
```

<210> SEQ ID NO 2
<211> LENGTH: 2250
<212> TYPE: DNA
<213> ORGANISM: Artificial Sequence
<220> FEATURE:

<223> OTHER INFORMATION: pMSV0 T-DNA

<400> SEQUENCE: 2

```
ggtctcatgc cggcgcgtgc cttgtcttcg tcgactagtc tagaagacaa gggaagcttt      60
agccgacgac ggaggttgag gctgagggat ggcagactgg gagctccaaa ctctatagta     120
tacctgtgcg ccttcgaaat ccgccgctcc cttgtcttat agtggttgtg aatgggccgg     180
accgggtcgg cccagcagga aaagaaggcg cgcactaata ttaccgcgcc ttcttttcct     240
gcgagggccc ggtagggccc gagcgatttg atgtaaagct tggtcctgct ttgtatgatt     300
tatctaaagc agcccattct aaagaaaccg gtcccgggca ctataaattg cctaacaagt     360
gcgattcatt ctgaataaaa actcccgttt tattatatct gatgaatgct gaaagcttac     420
attaatatgt cgtgcgatgg cacgaaaaaa cacacgcaat caatacaggg gggtagtagg     480
cgggcggcta agggtggtgc tcggcgggca gaacatcgaa aaatgcctga cacgccagtg     540
ccttaggcag gtgcgagtac gctcgacacc tgccgtaggg atccacgtct cagggatgaa     600
taaaaactcc cgttttatta tatctgatga atgctgaaag cttacattaa tatgtcgtgc     660
gatggcacga aaaacacac gcaatcaata caggggggta gtaggcgggc ggctaagggt     720
ggtgctcggc gggcagaaca tcgaaaaatc aagatctatc tgaatgtact gcctccgtag     780
gaggcagctc aggggagaa taccatttct ccccggcga cataatgtaa atgacgcagt      840
ttgcctcgaa atactccagc tgccctggag tcatttcctt catccaatct tcatccgagt     900
tggcgaggat tattgtaggc ttagacttct tctgcacctt cttcttctta ccatacttgg     960
ggtttacaat gaaatccctc tgacagccaa ctaactgttt ccaacaagga cagaatttaa    1020
acgggatatc atctacgatg ttgtagattg cgtcctcgtt gtatgaggac caatcaacat    1080
tatttgcca gtaattatga accctaggc ttctggccca agtagatttt cctgttcttg      1140
ttgggccgac gatgtagagg ctctgctttc ttgatctttc atctgatgac tggatacatt    1200
atccatccat tggaggtcag aaattgcatc ctcgagggta taacaggtag gttgaaggag    1260
catgtaagct tcgggactaa cctggaagat gttaggctgg agccaatcat tgattgactc    1320
attacaaagt aaatcaggtg aggattgcgg atgaggattg gtgaactctt cctgaatctc    1380
aggaaaaagc ttatttgcag agtattcaaa atactgcaat tttgtggacc aatcataggg    1440
aagctctttc tggatcatgg agaggtactc ttccttggaa gtagagtgtg aaataatgtc    1500
tcgcattatt tcatctttgg aaggcttttt ttccttaact tctgaatcag attttcctag    1560
gaaggggac ttcctaggaa tgaaagtacc tctctcaaac atagccagag gttccttgag     1620
gatgtaatcc ctcaccctgt ttactgactt ggcactctga atgtttgggt gaaacccatt    1680
aatatcaaag aaccttgagt ccgatattct taccggcttc tctgtttgaa gcaatgcatg    1740
taaatgcaaa cttccatctt tatgtgcctc tcgggcacat agaatgtact tgggaatcca    1800
acgaacaacg agctcccaga tcatctgaca ggcgatttca ggattttctg gacactttgg    1860
ataggtgagg aacgtgttag cgttccggtg tgagaactga cggttggatg aggaggaggc    1920
catgtttgag ccgacgacgg aggttgaggc tgagggatgg cagactggga gctccaaact    1980
ctatagtata cctgtgcgcc ttcgaaatcc gccgctccct tgtcttatag tggttgtgaa    2040
tgggccggac cgggtcggcc cagcaggaaa agaaggcgcg cactaatatt accgcgcctt    2100
cttttcctgc gagggcccgg tagggcccga gcgatttgat gtaaagcttg gtcctgcttt    2160
gtatgattta tctaaagcag cccattctaa agaaaccggt cccgggcact ataaattgcc    2220
taacaagtgc gattcattcg ggatgagacc                                     2250
```

<210> SEQ ID NO 3
<211> LENGTH: 1091
<212> TYPE: DNA
<213> ORGANISM: Artificial Sequence
<220> FEATURE:
<223> OTHER INFORMATION: modified Rep/RepA

<400> SEQUENCE: 3

| | |
|---|---|
| atgccttctg ctagtaagaa cttcagactc caatctaaat atgttttcct tacctatccc | 60 |
| aagtgctcat ctcaaagaga tgatttattc cagtttctct gggagaaact cacacctttt | 120 |
| cttattttct tccttggtgt tgcttctgag cttcatcaag atggcactac ccactatcat | 180 |
| gctcttctcc agcttgataa aaaccttgt attagggatc cttcttttt cgattttgaa | 240 |
| ggaaatcacc ctaatatcca gccagctaga aactctaaac aagtccttga ttacatatca | 300 |
| aaggacggag atattaaaac cagaggagat ttccgagatc ataaggtttc tcctcgcaaa | 360 |
| tctgacgcac gatggagaac tattatccag actgcaacgt ctaaggagga atatcttgac | 420 |
| atgatcaagg aagaattccc tcatgaatgg gcaacaaagc ttcaatggct ggaatattca | 480 |
| gccaacaaat tattccctcc acaacctgaa ccgtatgtgt cgcccttcac agaatcagat | 540 |
| cttcgctgcc acgaagatct acactcctgg agggaaaccc atctatacca tgtaagcata | 600 |
| gacgcttata cttacataca tcctgtctca taccaacaag ctcaatctga ccttgaatgg | 660 |
| atggccgatt taacaaggac aatggaagga atggaatccg acaccccagc ctctacatct | 720 |
| gcggaccaac tcgtaccgga agaccacct gggctagaag tctcggacga cacaactatt | 780 |
| ggaacggtac catcgatttc accaactacg atgaacacgc cacctataat atcatcgacg | 840 |
| acatcccctt caagttcgtc ccattgtgga agcaattaat aggttgccag tctgatttca | 900 |
| ctgtcaaccc taaatatgga aaaagaaga aaataaaagg tgggatccct tctataattc | 960 |
| tttgcaatcc tgacgaggac tggatgttat caatgacaag tcaacagaag gattacttta | 1020 |
| aagataattg cgtcacccac tacatgtgtg acggggagac tttttttgct cgggaatcgt | 1080 |
| cgagtcactg a | 1091 |

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4

| | |
|---|---|
| tgcgatgatc tacggtaaca aa | 22 |

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5

| | |
|---|---|
| gcgtgcaatc catcttgttc | 20 |

<210> SEQ ID NO 6
<211> LENGTH: 19
<212> TYPE: DNA
<213> ORGANISM: Artificial Sequence
<220> FEATURE:

```
<223> OTHER INFORMATION: primer

<400> SEQUENCE: 6
acgtaaggga tgacgcaca                                            19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
taccaccggt ccattcccta                                           20

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ggaaaatggc atcttgttcc c                                         21

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
ttgagatgag cacttgggat ag                                        22

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
acctcaacga cgcaagtatt                                           20
```